United States Patent [19]
Booij et al.

[11] Patent Number: 6,020,486
[45] Date of Patent: Feb. 1, 2000

[54] DEPOLYMERIZATION OF POLYAMIDES

[75] Inventors: Martin Booij, Sittar; Yvonne Helene Frentzen, Venlo, both of Netherlands; Bart Kurt Stefaan Hommez, Oostende; Eric Jozef Goethals, Ouwegem-Zingem, both of Belgium

[73] Assignee: DSM N.V., Heerlen, Netherlands

[21] Appl. No.: 09/115,234

[22] Filed: Jul. 14, 1998

[30] Foreign Application Priority Data

Jul. 14, 1997 [NL] Netherlands ............... 1006575

[51] Int. Cl.[7] .................................. C07D 201/12
[52] U.S. Cl. ............................................. 540/540
[58] Field of Search ............................. 540/540

[56] References Cited

U.S. PATENT DOCUMENTS 2,840,606  6/1958  Miller et al. ....................... 260/537
5,536,831  7/1996  Kopietz et al. ..................... 540/540

FOREIGN PATENT DOCUMENTS

| 12 35 924 | 3/1967 | Germany . |
| 52-113938 | 9/1977 | Japan . |
| 1017985 | 1/1966 | United Kingdom . |
| 94 08942 | 4/1994 | WIPO . |

*Primary Examiner*—Mukund J. Shah
*Assistant Examiner*—Bruck Kifle
*Attorney, Agent, or Firm*—Pillsbury Madison & Sutro Intellectual Property Group

[57] ABSTRACT

The invention relates to a process for depolymerising one or more polyamides in the presence of at least an aliphatic alcohol, the depolymerisation taking place with at most 40 mol. % catalyst. This process provides good selectivity towards the monomeric components of polyamides. This process moreover causes as few waste streams as possible.

15 Claims, No Drawings

DEPOLYMERIZATION OF POLYAMIDES

The invention relates to a process for depolymerising one or more polyamides in the presence of at least an aliphatic alcohol.

Such a process is already known from U.S. Pat. No. 2,840,606. This patent describes the depolymerisation of nylon 6,6 in the presence of an alcohol and sodium hydroxide, in which adipic acid and hexamethylene diamine are formed.

The drawback of this process is that a very large amount of caustic is required to enable the depolymerisation reaction to proceed. Acid is added after the depolymerisation. The adipic acid that is subsequently formed is then crystallised. These required amounts of caustic and acid lead to large streams of waste salt, which is disadvantageous for an industrial process.

Polyamides (such as production waste) have been reprocessed for about 40 years already. In particular this takes place at polyamide producers' and polyamide fibre spinners' plants. Over the past years product reprocessing has to an increasing extent been taking place at carpet producers' plants, too. Depolymerisation of polyamides is relevant for polyamide products in general and in particular in the case of carpets in which polyamides have been processed. In future, it will become increasingly important to reprocess carpet waste, both industrial carpet waste and the so-called post-consumer carpet waste, in an economic manner, partly because the dumping sites are approaching the limits of their capacity. The commercial feasibility of reprocessing carpet waste is of course directly dependent on the economic/technical possibility of converting these carpets, polyamide content into monomeric components that can be reused for the polymerisation, preferably directly, i.e. without further conversion reactions. There is therefore a need for further improvement of processes for reprocessing polyamide carpet waste.

The aim of the invention is to provide a process that causes as few waste streams as possible and moreover provides good selectivity towards the monomeric components of polyamides.

The monomeric components in the case of nylon 6 are caprolactam and caprolactam precursors. 'Precursors' are understood to be the compounds that can be used to prepare the polyamides without having to be converted first, for example amino caproic acid. In the case of nylon 6,6 the precursors are for example hexamethylene diamine and adipic acid.

This aim is achieved in that the depolymerisation takes place using at most 40 mol. % catalyst relative to the number of monomeric units in the polyamide to be depolymerised. Preferably the amount is between 5 and 30 mol. %, in particular between 10 and 20 mol. %.

This is surprising in view of the fact that the experimental results without excess catalyst, in this case sodium hydroxide, in U.S. Pat. No. 2,840,606 are substantially poorer than the results obtained with excess sodium hydroxide.

The following compounds are suitable for use as a catalyst: phosphoric acid, phosphorous acid, polyphosphoric acid, boric acid, sulphuric acid, hydrochloric acid, ammonium salts of these acids or alkali (earth) metal salts of the alcohols mentioned below.

The amounts of catalyst used in the process according to the invention lead to good reaction rates and the waste streams are substantially reduced. This implies a considerable saving in the variable costs and the costs of reprocessing the waste streams, considering the fact that a more than equimolar amount of caustic relative to the monomers in the polyamide is required in U.S. Pat. No. 2,840,606. It is furthermore necessary to add at least an equimolar amount of acid relative to the sodium adipate present in order to recover the adipic acid monomeric component.

The alcohols that are suitable for the is depolymerisation reaction are both monoalcohols and polyalcohols with 1–8C atoms, preferably with 1–4C atoms. Examples of suitable monoalcohols are methanol, ethanol, allyl alcohol, tert-butyl alcohol. Particularly suitable are/is methanol and/or ethanol. This is surprising in relation to U.S. Pat. No. 2,840,606 because that describes that poorer results, lower monomer yields, are obtained with ethanol. Examples of polyalcohols are ethylene glycol, propylene glycol, glycerol, pentaerythritol. Preferably use is made of ethylene glycol and/or propylene glycol.

When use is made of for example the sodium salt of ethylene glycol, this must be dissolved in a suitable polar solvent, for example one or more of the above alcohols. The sodium salt of ethylene glycol can also be obtained by dissolving metallic sodium in ethylene glycol.

The amount of alcohol required to effect depolymerisation of polyamide or polyamides lies between 1 and 100 parts by weight relative to the polyamide. Preferably the amount of alcohol is between 1 and 20 parts by weight relative to the polyamide, in particular between 1 and 10 parts by weight.

The depolymerisation can also be carried out in the presence of water. The amount of water is at most 50 wt. % relative to the polyamide, preferably at most 20 wt. %, in particular at most 10 wt. %. The polyamide often contains a little water; the process is generally carried out in the presence of more than 1 wt. % water relative to the polyamide.

The temperature at which the depolymerisation process according to the present invention can be carried out lies between 180° C. and the temperature at which the alcohol reaches its critical temperature. Preferably the temperature lies between 200 and 350° C.

Preferably the depolymerisation is carried out under conditions at which the monomeric components formed are extracted from the reacting mixture. This can take place by passing a gas through during the reaction, for example steam or nitrogen or the saturated alcohol vapour.

The alcohol can be separated from the monomeric components by means of techniques that are known per se. Examples of such techniques are distillation, steam distillation and vacuum distillation. The distillation can take place in one or more steps. The alcohol can then be returned to the depolymerisation reactor and be reused. The monomeric components can then be purified by means of for example distillation (steam or vacuum distillation), recrystallisation or other common purification techniques. Separation of any oligomers still present, because the depolymerisation reaction has for example not taken place in its entirety, of the monomeric components of the polyamide can also take place by means of cooling of the depolymerisation mixture or the addition of a non-solvent for the polymeric components. First the oligomers and the converted polymers will then crystallise/precipitate, as a result of which the monomeric components can be separated by means of filtration.

The process according to the present invention can be excellently used to process polyamide, products of, or containing, polyamides, in particular industrial carpet waste and post-consumer carpet waste. Preferably the carpet is first mechanically reduced by for example grinding, chopping, tearing and/or cutting with a knife and/or scissors. The majority of the carpet's non-polyamide components, for example latex (whether or not filled with $CaCO_3$), jute and/or polypropylene, can be separated from the carpet's polyamide portion in one or more separation steps. The carpet fragments can however also be fed to the reactor as such. According to another preferred embodiment the back of the carpet, into which the carpet fibres are applied, is separated from the carpet fibres as much as possible. This can be done with the aid of hydroclones. The process according to the invention leads to good results with only 10% polyamide in the reactor in addition to other components.

EXAMPLE I 10 g of polyamide-6 and 90 g of methanol were introduced into a 250-ml autoclave. The autoclave contents were heated to 230° C. The degree of conversion to monomeric components of polyamide-6 was determined with the aid of HPLC from Kontron® Instruments using a Nucleosil® 120–5 C18 column from Macherey-Nagel. The detector was a diode array detector from Kontron® Instruments. After 1 hour at this temperature a sample was taken from the autoclave and immediately cooled to room temperature. The degree of conversion to monomeric components of polyamide-6 was 11.5%.

EXAMPLE II 80 g of nylon-6 and 220 g of ethylene glycol were introduced into a 600-$cm^3$ titanium reactor fitted with a magnetic stirrer and a sampling point. The reactor was heated to 275° C. 7 g of phosphoric acid was dissolved in ethylene glycol (total 100 g) and introduced into the reactor. The reactor temperature was kept at 250° C. Samples were taken after 16, 36 and 232 minutes. The results are given in Table I.

Example III

Example II was repeated. The amount of phosphoric acid was 14 g. The results are given in Table I.

EXAMPLE IV

Example II was repeated using an amount of phosphoric acid of 28 g. The results are given in Table I.

TABLE I

| Example II | | Example III | | Example IV | |
| --- | --- | --- | --- | --- | --- |
| time (min.) | degree of conversion to caprolactam (%) | time (min.) | degree of conversion to caprolactam (%) | time (min.) | degree of conversion to caprolactam (%) |
| 16 | 8.5 | 11 | 10.4 | 17 | 21.8 |
| 36 | 18.1 | 43 | 25.8 | 37 | 24.4 |
| 232 | 37 | 161 | 29.3 | 67 | 27.1 |

EXAMPLE V

Example II was repeated. After the reactor had reached a temperature of 275° C., 11.7 g of polyphosphoric acid dissolved in 88.3 g of ethylene glycol was fed to the reactor. The reactor temperature was kept at 250° C. After 151 minutes the degree of conversion to caprolactam was 32.5%

EXAMPLE VI

Example II was repeated. 270 g of ethylene glycol was introduced into the reactor. After 275° C. had been reached 5.4 g of phosphorous acid dissolved in 44.6 g of ethylene glycol was fed to the reactor. The reactor temperature was then kept at 250° C. The degree of conversion to caprolactam after 225 minutes was 31%.

EXAMPLE VII 80 g of nylon-6 and 270 g of ethylene glycol were introduced into a reactor as in Example II. After the reactor had reached a temperature of 275° C., 1.6 g of metallic sodium dissolved in 48.4 g of ethylene glycol with the formation of 5.8 g of sodium glycolate was introduced into the reactor. The temperature was kept at 250° C. The conversion results after 22, 97 and 172 minutes are given in Table II.

EXAMPLE VIII

Example VII was repeated. 3.2 g of metallic sodium dissolved in 46.7 g of ethylene glycol was introduced into the reactor. The conversion results after 17, 82 and 142 minutes are given in Table II.

TABLE II

| Example VII | | Example VIII | |
| --- | --- | --- | --- |
| time (min.) | degree of conversion to caprolactam (%) | time (min.) | degree of conversion to caprolactam (%) |
| 22 | 5 | 17 | 7 |
| 97 | 16 | 82 | 20 |
| 172 | 22 | 142 | 27 |

We claim:

1. A process for depolymerising one or more polyamides in the presence of at least an aliphatic alcohol, the depolymerisation taking place with at most 40 mol. % catalyst, wherein said catalyst is selected from the group consisting of phosphoric acid, phosphorous acid, polyphosphoric acid, boric acid, sulphuric acid, hydrochloric acid, ammonium salt of phosphoric acid, ammonium salt of phosphorous acid, ammonium salt of polyphosphoric acid, ammonium salt of boric acid, ammonium salt of sulphuric acid, ammonium salt of hydrochloric acid, or an alkali (earth) metal salt of an alcohol.

2. The process according to claim 1, wherein between 5 and 30 mol. % catalyst is present.

3. The process according to claim 1 or claim 2, wherein the catalyst is phosphoric acid or phosphorous acid.

4. The process according to claim 1 or claim 2, wherein the catalyst is an alkali (earth) metal salt of an alcohol.

5. The process according to claim 1, wherein the aliphatic alcohol has 1–4 C atoms.

6. The process according to claim 5, wherein the aliphatic alcohol is methanol, and/or ethanol.

7. The process according to claim 5, wherein the aliphatic alcohol is ethylene glycol.

8. The process according to claim 1, wherein the amount of aliphatic alcohol is between 1 and 100 parts by weight relative to the polyamide or polyamides.

9. The process according to claim 8, wherein the amount of aliphatic alcohol is between 1 and 20 parts by weight.

10. The process according to claim 9, wherein the amount of aliphatic alcohol is between 1 and 10 parts by weight.

11. The process according to claim 1, wherein the depolymerisation is carried out in the presence of at most 50 wt. % water relative to the polyamide or polyamides.

12. The process according to claim 1, wherein alcohol of the caprolactam obtained is separated and reused in the depolymerisation.

13. The process according to claim 1, wherein the depolymerisation takes place at a temperature of between 180 and 400° C.

14. The process according to claim 13, wherein the depolymerisation takes place at a temperature of between 200 and 350° C.

15. The process according to claim 1, wherein carpet waste containing polyamide is used in the depolymerisation.

* * * * *